US00PP24044P2

(12) United States Plant Patent
Marczyński

(10) Patent No.: US PP24,044 P2
(45) Date of Patent: Nov. 26, 2013

(54) ***CLEMATIS* PLANT NAMED 'SWEET SUMMER LOVE'**

(50) Latin Name: *Clematis hybrida*
Varietal Denomination: Sweet Summer Love

(75) Inventor: Szczepan Marczyński, Pruszków (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 84 days.

(21) Appl. No.: 13/385,293

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — C. A. Whealy

(57) ABSTRACT

A new and distinct cultivar of *Clematis* plant named 'Sweet Summer Love' characterized by its upright and vining plant habit; relatively small leaves; freely flowering habit; long flowering period; and single fragrant flowers that are red purple and purple in color.

2 Drawing Sheets

Botanical designation: *Clematis hybrida.*
Cultivar denomination: 'SWEET SUMMER LOVE'.

BACKGROUND OF THE INVENTION

The present invention relates to a new and distinct cultivar of *Clematis* plant, botanically known as *Clematis hybrida* and hereinafter referred to by the name 'Sweet Summer Love'.

The new *Clematis* plant is a product of a planned breeding program conducted by the Inventor in Pruszków, Poland. The objective of the breeding program is to create new *Clematis* plants with fragrant purple-colored flowers.

The new *Clematis* plant originated from a cross-pollination conducted by the Inventor in July, 2003 in Pruszków, Poland of an unidentified selection of *Clematis hybrida*, not patented, as the female, or seed parent with an unidentified selection of *Clematis hybrida*, not patented, as the male, or pollen, parent. The new *Clematis* plant was discovered and selected by the Inventor as a single flowering plant from within the progeny of the stated cross-pollination in a controlled environment in Pruszków, Poland.

Asexual reproduction of the new *Clematis* plant by cuttings in Pruszków, Poland since June, 2004 has shown that the unique features of this new *Clematis* plant are stable and reproduced true to type in successive generations.

SUMMARY OF THE INVENTION

Plants of the new *Clematis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sweet Summer Love'. These characteristics in combination distinguish 'Sweet Summer Love' as a new and distinct *Clematis* plant:

1. Upright and vining plant habit.
2. Relatively small leaves.
3. Freely flowering habit.

4. Long flowering period.
5. Single fragrant flowers that are red purple and purple in color.

Plants of the new *Clematis* differ primarily from plants of the parent selections in flower color.

Plants of the new *Clematis* can be compared to plants of the *Clematis* 'Rubromarginata', not patented. Plants of the new *Clematis* differ primarily from plants of 'Rubromarginata' in the following characteristics:

1. Plants of the new *Clematis* are more compact than plants of 'Rubromarginata'.
2. Plants of the new *Clematis* flower for a longer period of time than plants of 'Rubromarginata'.
3. Plants of the new *Clematis* are more freely flowering than plants of 'Rubromarginata'.
4. Plants of the new *Clematis* and 'Rubromarginata' differ in flower color.

BRIEF DESCRIPTION OF THE PHOTOGRAPHS

The accompanying colored photographs illustrate the overall appearance of the new *Clematis* plant showing the colors as true as it is reasonably possible to obtain in colored reproductions of this type. Colors in the photographs may differ slightly from the color values cited in the detailed botanical description which accurately describe the actual colors of the new *Clematis* plant.

The photograph on the first sheet comprises a side perspective view of a typical flowering plant of 'Sweet Summer Love' grown in a container.

The photograph on the second sheet is a close-up view of a typical flowering plant of 'Sweet Summer Love'.

DETAILED BOTANICAL DESCRIPTION

Plants used for the aforementioned photographs and following description were grown during the summer in an outdoor nursery in Pruszków, Poland and under cultural practices which closely approximate commercial production. During the production of the plants, day temperatures ranged from 18° C. to 23° C. and night temperatures ranged from 13° C. to 16° C. Plants were three years old when the photograph and the description were taken. In the following description, color references are made to The Royal Horticultural Society Colour Chart, 1995 Edition, except where general terms of ordinary dictionary significance are used.

Botanical classification: *Clematis hybrida* 'Sweet Summer Love'.

Parentage:

*Female, or seed, parent*.—Unidentified selection of *Clematis hybrida*, not patented.

*Male, or pollen, parent*.—Unidentified selection of *Clematis hybrida*, not patented.

Propagation:

*Type*.—By cuttings.

*Time to initiate roots, summer*.—About two weeks.

*Time to produce a rooted young plant, summer*.—About one to three months.

*Root description*.—Fine to thick; color, close to 164B.

*Rooting habit*.—Freely branching.

Plant description:

*Plant and growth habit*.—Perennial vine; upright and vining plant habit; vigorous growth habit.

*Plant height*.—About 200 cm to 250 cm.

*Plant width*.—About 150 cm to 200 cm.

*Lateral branch description*.—Branching habit: Freely branching habit, about 21 lateral branches develop per plant. Length: About 45 cm to 55 cm. Diameter: About 2 mm. Internode length: About 5 cm to 7 cm. Texture, developing: Slightly pubescent. Texture, developed: Smooth, glabrous. Color, developing: Close to 144A tinged with close to 70A. Color, developed: Close to 175A.

Foliage description:

*Arrangement*.—Opposite, compound with five to seven leaflets.

*Length, leaf*.—About 12 cm to 15 cm.

*Length, leaflet*.—About 2 cm to 6 cm.

*Width, leaf*.—About 10 cm to 12 cm.

*Width, leaflet*.—About 2 cm to 4 cm.

*Shape, leaflet*.—Ovate.

*Apex, leaflet*.—Acute.

*Base, leaflet*.—Truncate.

*Margin, leaflet*.—Entire.

*Texture, leaflet, upper and lower surfaces*.—Smooth, glabrous.

*Venation pattern, leaflet*.—Pinnate.

*Color, leaflet*.—Developing, upper surface: Close to 137A. Developing, lower surface: Close to 138A. Fully expanded, upper surface: Close to 139A; venation, close to 139A. Fully expanded, lower surface: Close to 137B; venation, close to 137B.

*Petioles*.—Length, leaflets: About 4 cm to 4.5 cm. Diameter, leaflets: About 1 mm. Color, leaflets, upper and lower surfaces: Close to 144A.

Flower description:

*Flower shape, arrangement and flowering habit*.—Single star-shaped terminal and axillary flowers; flowers face outwardly; freely flowering habit, about 2,500 flowers develop per plant.

*Natural flowering season*.—Continuous flowering from July to end of August in Poland.

*Flower longevity on the plant*.—About eight to ten days; flowers not persistent.

*Fragrance*.—Present, pleasant.

*Flower buds*.—Length: About 1 cm to 1.5 cm. Diameter: About 5 mm to 7 mm. Shape: Narrowly ovate. Color: Close to 145C.

*Flower diameter*.—About 4.5 cm to 5 cm.

*Petals*.—None observed.

*Sepals*.—Arrangement: About four to five in a single whorl. Length: About 2 cm to 2.5 cm. Width: About 1 cm. Shape: Obovate to oblanceolate. Apex: Bluntly obtuse. Base: Narrowly cuneate. Margin: Entire, irregularly dentate; undulate. Texture, upper and lower surfaces: Smooth, glabrous. Color: When opening, upper surface: Close to 61A. When opening, lower surface: Close to 61A; central stripe, close to 155A. Fully opened, upper surface: Close to 61A; center, close to 77A. Fully opened, lower surface: Close to 61A; central stripe, close to 155A.

*Peduncles*.—Length: About 9 cm to 15 cm. Diameter: About 2 mm to 3 mm. Strength: Strong. Texture: Smooth, glabrous. Color: Close to 144B.

*Reproductive organs*.—Stamens: Quantity per flower: About 30. Anther shape: Lanceolate. Pollen color: Close to 63D. Pistils: Quantity per flower: About 16 to 20. Pistil length: About 1 cm. Stigma shape: Conical, narrow. Stigma color: Close to 145C. Style length: About 6 mm. Style color: Close to 145C. Ovary color: Close to 145C.

*Seeds*.—Seed development has not been observed on plants of the new *Clematis*.

Disease & pest resistance: Plants of the new *Clematis* have not been noted to be resistant to pathogens and pests common to *Clematis* plants.

Garden performance: Plants of the new *Clematis* have exhibited good tolerance to rain and wind and have been observed to be suitable for USDA Hardiness Zone 5 and USDA Heat Zone 9.

It is claimed:

1. A new and distinct *Clematis* plant named 'Sweet Summer Love' as illustrated and described.

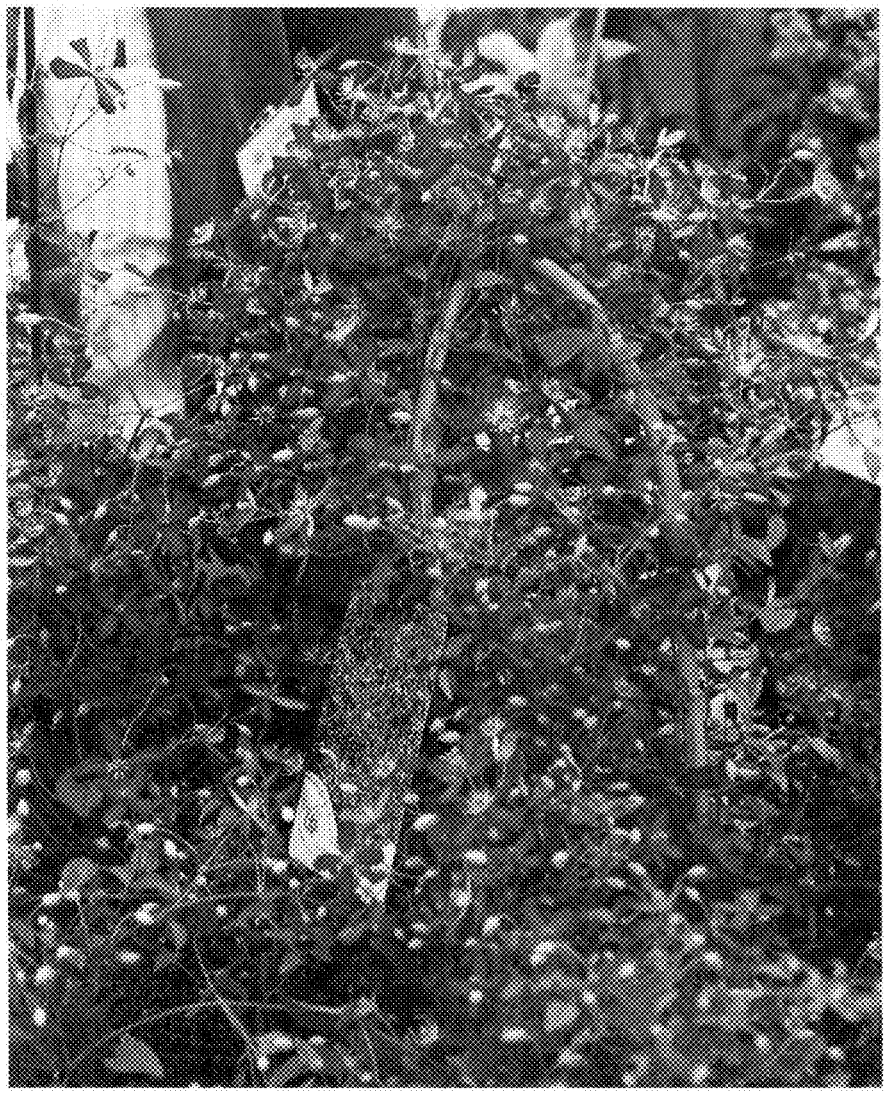

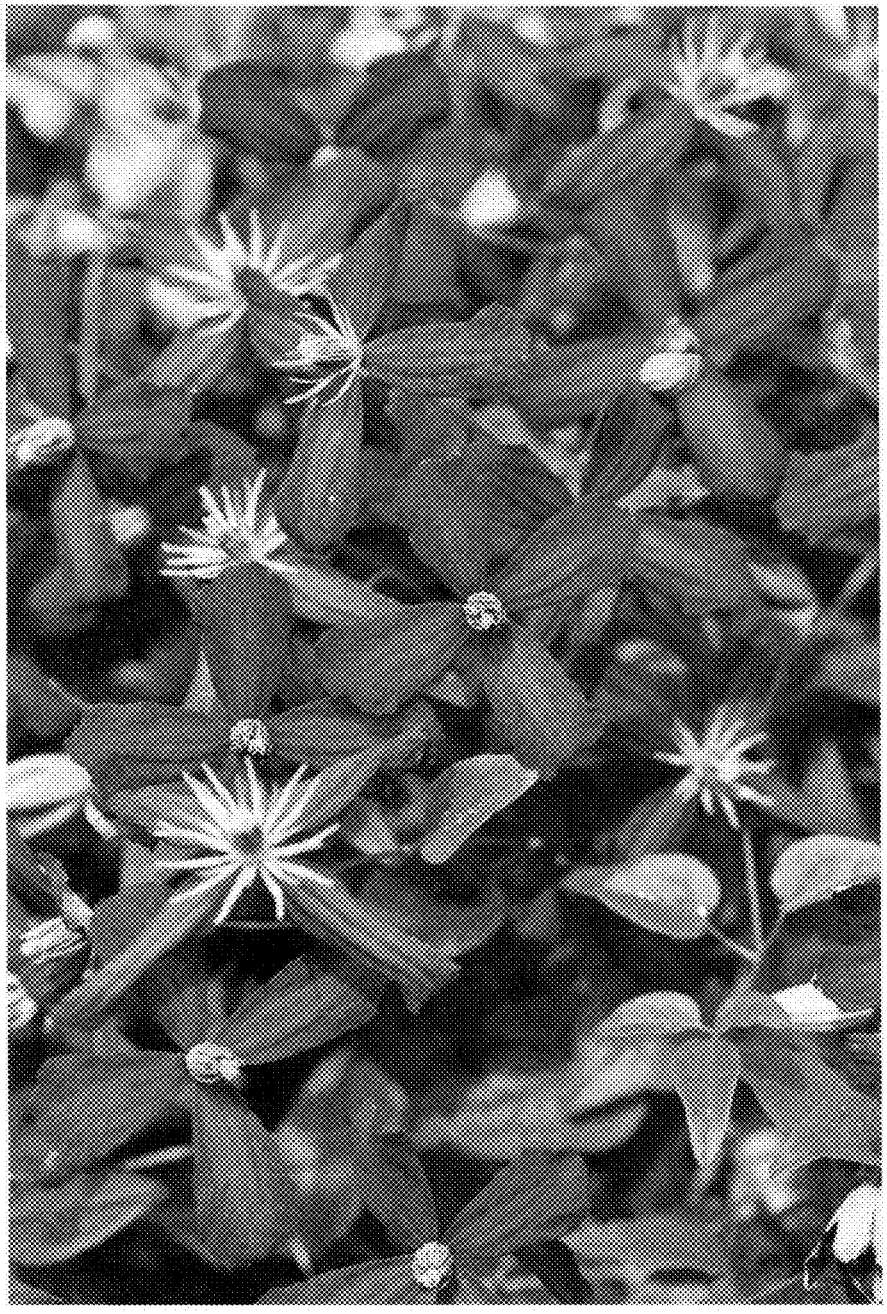

* * * * *